United States Patent [19]

Jahn et al.

[11] Patent Number: 4,956,003

[45] Date of Patent: Sep. 11, 1990

[54] CYCLOHEXANE-1,3-DIONE DERIVATIVES AND THEIR USE FOR CONTROLLING UNDESIRED PLANT GROWTH

[75] Inventors: Dieter Jahn, Neckarhausen; Rainer Becker, Bad Durkheim; Norbert Goetz, Worms; Bruno Wuerzer, Otterstadt, all of Fed. Rep. of Germany

[73] Assignee: BASF Aktiengesellschaft, Ludwigshafen, Fed. Rep. of Germany

[21] Appl. No.: 328,573

[22] Filed: Mar. 27, 1989

Related U.S. Application Data

[60] Division of Ser. No. 13,180, Feb. 9, 1987, Pat. No. 4,851,032, which is a continuation of Ser. No. 612,632, May 21, 1984, abandoned, which is a continuation of Ser. No. 461,748, Jan. 28, 1983, abandoned, which is a continuation of Ser. No. 382,307, May 27, 1982, abandoned.

[30] Foreign Application Priority Data

May 29, 1981 [DE] Fed. Rep. of Germany ....... 3121355
Jun. 12, 1981 [DE] Fed. Rep. of Germany ....... 3123312

[51] Int. Cl.$^5$ ............... A01N 43/36; C07D 207/323
[52] U.S. Cl. ........................................ 71/92; 71/94; 71/95; 544/239; 544/240; 544/241; 544/316; 544/311; 544/334; 544/335; 546/296; 546/300; 546/335; 546/338; 548/375; 548/376; 548/378; 548/544; 548/545; 548/546; 548/550; 548/561

[58] Field of Search ............... 71/92; 548/378, 375, 548/376

[56] References Cited

U.S. PATENT DOCUMENTS 4,863,504 9/1989 Hamaguchi et al. ............... 548/378

OTHER PUBLICATIONS

Jahn et al., "Chemical Abstracts", vol. 98, 1982, col. 98:160705k.
Jahn et al., "Chemical Abstracts", vol. 100, 1983, col. 100:169948j.

*Primary Examiner*—Glennon H. Hollrah
*Assistant Examiner*—James H. Turnipseed
*Attorney, Agent, or Firm*—Keil & Weinkauf

[57] ABSTRACT

Cyclohexane-1,3-dione derivatives of the formula

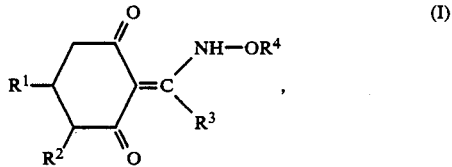

where $R^1$, $R^2$, $R^3$ and $R^4$ have the meanings given in the disclosure, and the use thereof for combating unwanted plants, especially Gramineae.

8 Claims, No Drawings

CYCLOHEXANE-1,3-DIONE DERIVATIVES AND THEIR USE FOR CONTROLLING UNDESIRED PLANT GROWTH

This is a division of Ser. No. 013,180 filed 2-9-87, now U.S. Pat. No. 4,851,032, which is a continuation of Ser. No. 06/612,632, filed 5/21/84, abandoned which is a continuation of Ser. No. 06/461,748, filed 1/28/83, abandoned which is a continuation of Ser. No. 06/382,307, filed 5/27/82 abandoned.

The present invention relates to cyclohexane-1,3-dione derivatives, a process for their preparation, and herbicides which contain these compounds as active ingredients.

It has been disclosed that cyclohexane-1,3-dione derivatives are useful herbicides for selectively controlling the growth of undesired grasses in broad-leaved crops (German Published Application DAS No. 2,439,104).

We have found that cyclohexane-1,3-dione derivatives of the formula

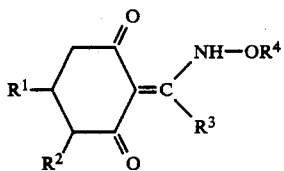

(I)

where $R^1$ is a five-membered or six-membered aromatic heterocyclic radical which contains one or two nitrogen atoms and may carry one or two substituents from the group comprising alkyl, halogen, alkoxy and dialkylamino, $R^2$ is hydrogen, methoxycarbonyl or ethoxycarbonyl, $R^3$ is alkyl of 1 to 4 carbon atoms, and $R^4$ is alkyl of 1 to 3 carbon atoms, alkenyl of 3 or 4 carbon atoms, haloalkenyl of 3 or 4 carbon atoms and 1 to 3 halogen atoms, or propargyl, and salts of these compounds, have a surprisingly powerful and superior herbicidal action against plant species from the family of the grasses (Gramineae) but are well tolerated by broad-leaved crops and other crops which do not belong to the family of the Gramineae.

The compounds of the formula I can occur in several tautomeric forms, all of which are embraced by the claim:

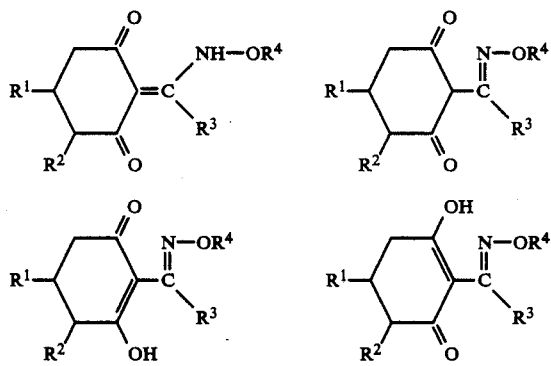

$R^1$ in formula I, is a five-membered or six-membered aromatic heterocyclic radical, e.g. pyridyl, pyrimidyl, pyrazinyl, pyridazinyl, pyrrolyl, imidazolyl or pyrazolyl, which may carry one or two substituents. Suitable substituents are halogen, e.g. chlorine or iodine, alkyl or alkoxy of 1 or 2 carbon atoms, e.g. methyl, ethyl, methoxy or ethoxy, or dialkylamino where alkyl is of 1 to 4 carbon atoms, e.g. dimethylamino or diethylamino.

Examples of radicals $R^1$ are pyrid-2-yl, pyrid-3-yl, pyrid-4-yl, 2-chloropyrid-3-yl, 2-chloropyrid-4-yl, 2-chloropyrid-5-yl, 2-chloropyrid-6-yl, 2-methylpyrid-6-yl, 2-methylpyrid-5-yl, 3-methylpyrid-4-yl, 4-methylpyrid-3-yl, 2,6-dimethylpyrid-4-yl, 2,4-dimethylpyrid-6-yl, pyrrol-2-yl, N-methylpyrrol-2-yl, N-methylpyrazol-2-yl and N-methylpyrazol-4-yl.

$R^3$ in formula I, is straight-chain or branched alkyl of 1 to 4 carbon atoms, e.g. methyl, ethyl, n-propyl, i-propyl, n-butyl, sec.-butyl, i-butyl or tert.-butyl.

$R^4$ in formula I, is alkyl of 1 to 3 carbon atoms, alkenyl of 3 or 4 carbon atoms or haloalkenyl of 3 or 4 carbon atoms, which carries up to three halogen substituents, e.g. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl, 1,1,2-trichloroprop-1-en-3-yl or propargyl.

Examples of suitable salts of the compounds of the formula I are the alkali metal salts, in particular the potassium, sodium, manganese, copper, zinc, iron and barium salts.

Preferred compounds of the formula I are those where $R^1$ is pyrid-3-yl, $R^2$ is hydrogen, $R^3$ is alkyl, chosen from the group comprising ethyl, n-propyl and i-propyl, and $R^4$ is ethyl or allyl.

The compounds of the formula I may be obtained by reacting a compound of the formula

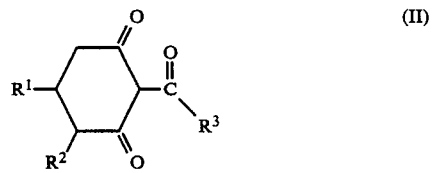

(II)

where $R^1$, $R^2$ and $R^3$ have the above meanings, with a hydroxylamine derivative $R^4O$—$NH_3Y$, where $R^4$ has the above meanings and Y is an anion.

The reaction is advantageously carried out in the heterogeneous phase in an inert diluent at from 0° to 80° C., or from 0° C. to the boiling point of the reaction mixture, in the presence of a base. Examples of suitable bases are carbonates, bicarbonates, acetates, alcoholates, hydroxides and oxides of alkali metals and of alkaline earth metals, in particular of sodium, potassium, magnesium and calcium. In addition, organic bases, e.g. pyridine or tertiary amines, may also be used.

A pH of from 2 to 7, in particular from 4.5 to 5.5, is particularly advantageous for the reaction, and may advantageously be established by adding an acetate, for example an alkali metal acetate, in particular sodium acetate or potassium acetate, or a mixture of the two. For example, from 0.5 to 2 moles, based on the ammonium compound of the formula $R^4O$—$NH_3Y$, of the alkali metal acetate are added.

Examples of suitable solvents are dimethylsulfoxide, alcohols, e.g. methanol, ethanol and isopropanol, benzene, chlorohydrocarbons, e.g. chloroform and dichloroethane, esters, e.g. ethyl actate, and ethers, e.g. dioxane and tetrahydrofuran.

The reaction is complete after a few hours, and the product may be isolated by concentrating the mixture, adding water, extracting the mixture with a non-polar solvent, e.g. methylene chloride, and distilling off the solvent under reduced pressure.

The compounds of the formula I may also be obtained by reacting a compound of the formula II with a hydroxylamine of the formula $R^4O-NH_2$, where $R^4$ has the above meanings, in an inert diluent at from 0° C. to the boiling point of the reaction mixture, in particular from 15° to 70° C.

Examples of suitable solvents for this reaction are alcohols, e.g. methanol, ethanol, isopropanol and cyclohexanol, hydrocarbons which may or may not be chlorinated, e.g. methylene chloride, toluene and dichloroethane, esters, e.g. ethyl acetate, nitriles, e.g. acetonitrile, and cyclic ethers, e.g. tetrahydrofuran.

The alkali metal salts of the compounds of the formula I may be obtained by treating these compounds with sodium hydroxide or potassium hydroxide in aqueous solution or in an organic solvent, e.g. methanol, ethanol or acetone. Sodium alcoholate or potassium alcoholate may also be used as the base.

The other metal salts, e.g. the manganese, copper, zinc, iron and barium salts, may be prepared by reacting the sodium salt with the appropriate metal chloride in aqueous solution.

The compounds of the formula II may be prepared from cyclohexane-1,3-diones of the formula III, which can also be present in the tautomeric forms of formulae IIIa/IIIb, by conventional methods (Tetrahedron Letters, 29 (1975), 2491).

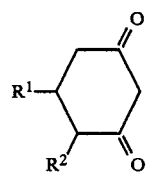
(III)

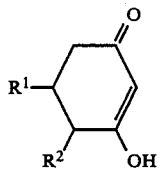
(IIIa)

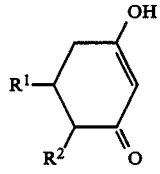
(IIIb)

It is also possible to prepare a compound of the formula II via the intermediate stage of the enol ester, which may be produced as an isomer mixture in the conversion of a compound of the formula III, and undergoes rearrangement in the presence of an imidazole or pyridine derivative (Japanese Preliminary Published Application No. 54/063052).

The compounds of the formula III may be prepared by conventional processes, as can be seen from the scheme below:

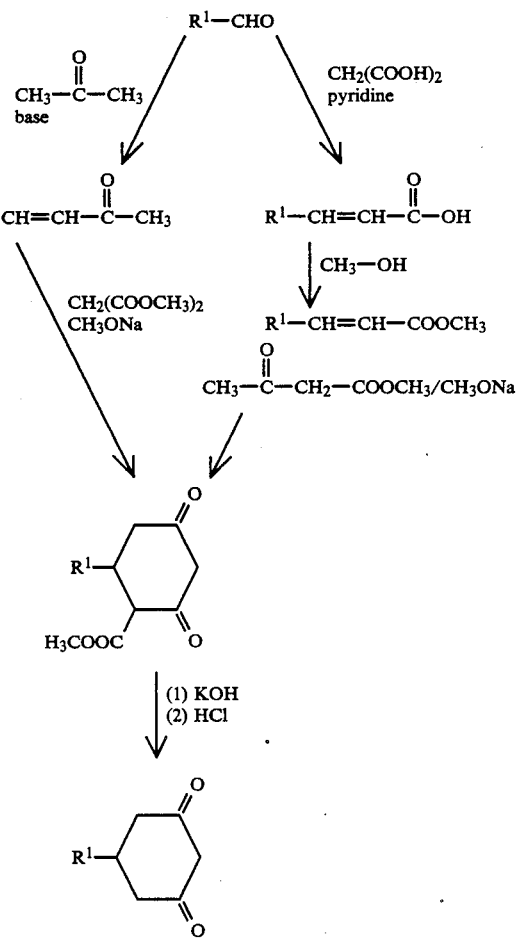

Cyclohexane-1,3-dione derivatives of the formula I are obtained as described in the Examples below, in which parts by weight bear the same relation to parts by volume as that of the kilogram to the liter.

EXAMPLE 1

3.1 parts by weight of ethoxyammonium chloride, 7.8 parts by weight of 2-butyryl-5-(pyrid-3-yl)-cyclohexane-1,3-dione, 2.7 parts by weight of anhydrous sodium acetate and 100 parts by volume of ethanol were stirred at room temperature for 12 hours. The solvent was distilled off under reduced pressure, the residue was stirred with 120 parts of water and 100 parts of methylene chloride, the organic phase was separated off, the aqueous phase was extracted with 50 parts of methylene chloride, and the combined organic phases were washed with water, dried over sodium sulfate and concentrated under reduced pressure. An oil which gradually solidified was obtained. The solid was stirred with diethyl ether, the residue was filtered off under suction, and 2-ethoxyaminobutylidene-5-(pyrid-3-yl)-cyclohexane-1,3-dione of melting point 80°-82° C. was obtained in a yield corresponding to 90% of theory (active ingredient No. 1).

$C_{17}H_{22}N_2O_3$ (302); calculated: C 67.53, H 7.3, N 9.26; found: C 67.3, H 7.2, N 9.3.

EXAMPLE 2

2.2 parts by weight of allyloxyamine, 7.8 parts by weight of 2-butyryl-5-(pyrid-3-yl)-cyclohexane-1,3- dione and 100 parts by volume of ethanol were stirred at room temperature for 12 hours. The solvent was distilled off under reduced pressure, the residue was taken up in 200 parts of methylene chloride, the solution was washed twice with water and dried over sodium sulfate, and the solvent was distilled off under reduced pressure. An oil which gradually solidified was obtained. The solid was stirred with diethyl ether, the residue was filtered off under suction, and 2-allyloxyaminobutylidene-5-(pyrid-3-yl)-cyclohexane-1,3-dione of melting point 87°–91° C. was obtained in a yield corresponding to 94% of theory (active ingredient No. 2).

$C_{18}H_{22}N_2O_3$ (314): calculated: C 68.77, H 7.05, N 8.91; found: C 68.3, H 6.9, N 9.0.

The following compounds may be obtained in the same manner:

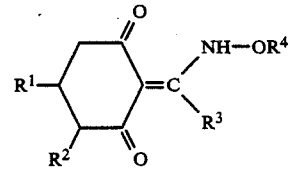

| No. | $R^1$ | $R^2$ | $R^3$ | $R^4$ | $n_D$/m.p. [°C.] |
|---|---|---|---|---|---|
| 3 | Pyrid-3-yl | H | $C_2H_5$ | $C_2H_5$ | 76–78 |
| 4 | " | H | $C_2H_5$ | —$CH_2$—CH=$CH_2$ | 81–83 |
| 5 | " | H | $CH_3$ | $C_2H_5$ | 65–69 |
| 6 | " | H | $CH_3$ | —$CH_2$—CH=$CH_2$ | 87–89 |
| 7 | " | H | n-$C_3H_7$ | —$CH_2$—C≡CH | |
| 8 | " | H | n-$C_3H_7$ | —$CH_2$—C=CHCl | |
| 9 | " | $COOCH_3$ | n-$C_3H_7$ | —$CH_2$—CH=$CH_2$ | |
| 10 | Pyrid-2-yl | H | n-$C_3H_7$ | $C_2H_5$ | $n_D^{22}$ 1.549 |
| 11 | " | H | n-$C_3H_7$ | —$CH_2$—CH=$CH_2$ | $n_D^{22}$ 1.556 |
| 12 | 6-Methylpyrid-2-yl | H | n-$C_3H_7$ | $C_2H_5$ | $n_D^{24}$ 1.551 |
| 13 | " | H | n-$C_3H_7$ | —$CH_2$—CH=$CH_2$ | $n_D^{24}$ .1556 |
| 14 | " | H | $C_2H_5$ | $C_2H_5$ | $n_D^{24}$ 1.556 |
| 15 | " | H | $C_2H_5$ | —$CH_2$—CH=$CH_2$ | $n_D^{24}$ 1.561 |
| 16 | Pyrrol-2-yl | H | n-$C_3H_7$ | $C_2H_5$ | |
| 17 | " | H | n-$C_3H_7$ | —$CH_2$—CH=$CH_2$ | |
| 18 | N-Methylpyrrol-2-yl | H | n-$C_3H_7$ | $C_2H_5$ | $n_D^{23}$ 1.556 |
| 19 | " | H | n-$C_3H_7$ | —$CH_2CH$=$CH_2$ | $n_D^{23}$ 1.560 |
| 20 | N-Methylpyrazol-3-yl | H | n-$C_3H_7$ | $C_2H_5$ | |
| 21 | " | H | " | —$CH_2$—CH=$CH_2$ | |
| 22 | N-Methylpyrazol-4-yl | H | " | $C_2H_5$ | |
| 23 | " | H | " | —$CH_2$—CH=$CH_2$ | |
| 24 | 4-Methylpyrid-3-yl | H | " | $C_2H_5$ | |
| 25 | " | H | " | —$CH_2$—CH=$CH_2$ | |
| 26 | Pyrid-3-yl (sodium salt) | H | " | $C_2H_5$ | 164–168 |
| 27 | " | H | " | —$CH_2$—CH=$CH_2$ | 116–121 |
| 28 | Pyrid-4-yl | H | $C_2H_5$ | $C_2H_5$ | |
| 29 | " | H | n-$C_3H_7$ | $C_2H_5$ | 80–85 |
| 30 | " | H | " | —$CH_2$—CH=$CH_2$ | |
| 31 | Pyrid-3-yl (sodium salt) | H | $C_2H_5$ | $C_2H_5$ | 105–109 (decomposition) |
| 32 | Pyrid-3-yl (sodium salt) | H | " | —$CH_2$—CH=$CH_2$ | |
| 33 | Pyrid-3-yl (potassium salt) | H | n-$C_3H_7$ | $C_2H_5$ | |
| 34 | Pyrid-3-yl (copper salt) | H | " | " | |
| 35 | Pyrid-3-yl (calcium salt) | H | " | " | |
| 36 | Pyrid-3-yl (iron salt) | H | " | " | |
| 37 | Pyrimid-5-yl | H | " | " | 57–60 |
| 38 | " | H | H | —$CH_2$—CH=$CH_2$ | $n_D^{24}$ 1.5616 |
| 39 | 2-Methoxypyrimid-5-yl | H | n-$C_3H_7$ | —$CH_2$—CH=$CH_2$ | |
| 40 | " | H | " | $C_2H_5$ | |
| 41 | " | H | " | —$CH_2$—CH=$CH_2$ | |
| 42 | 4,6-Dimethoxypyrimid-5-yl | H | " | " | |
| 43 | " | H | " | $C_2H_5$ | |
| 44 | Pyrid-3-yl | H | " | —$CH_2$—CH=CHCl | |
| 45 | Pyrid-2-yl | H | " | " | $n_D^{21}$: 1.568 |
| 46 | 1-Methylpyrrol-2-yl | $COOCH_3$ | " | $C_2H_5$ | 98-1-Methylpyrrol-2-yl |
| 47 | 1-Methylpyrrol-2-yl (sodium salt) | " | " | " | |
| 48 | 1-Methylpyrrol-2-yl | H | $C_2H_5$ | " | |
| 49 | 1-Methylpyrrol-2-yl | H | " | —$CH_2$—CH=$CH_2$ | |
| 50 | 1-Methylpyrrol-2-yl (sodium salt) | H | " | " | |
| 51 | 1-Methylpyrrol-2-yl (sodium salt) | H | " | $C_2H_5$ | |
| 52 | 1-Methylpyrrol-3-yl | H | " | " | |
| 53 | 1-Methylpyrrol-3-yl | H | " | —$CH_2$—CH=$CH_2$ | |
| 54 | 1-Methylpyrrol-3-yl | H | n-$C_3H_7$ | " | |
| 55 | 1-Methylpyrrol-3-yl | H | " | $C_2H_5$ | " |
| 56 | 1-Methylpyrrol-3-yl (sodium salt) | H | " | " | |
| 57 | 1-Methylpyrrol-3-yl (sodium salt) | H | " | —$CH_2$—CH=$CH_2$ | |
| 58 | 1-Methylpyrrol-3-yl (sodium salt) | H | $C_2H_5$ | $C_2H_5$ | |

-continued

| No. | R$^1$ | R$^2$ | R$^3$ | R$^4$ | n$_D$/m.p. [°C.] |
|---|---|---|---|---|---|
| 59 | 1-Methylpyrrol-3-yl (sodium salt) | H | " | —CH$_2$—CH=CH$_2$ | |
| 60 | 1-Isopropylpyrrol-3-yl | H | " | " | |
| 61 | 1-Isopropylpyrrol-3-yl | H | " | C$_2$H$_5$ | |
| 62 | 1-Isopropylpyrrol-3-yl | H | n-C$_3$H$_7$ | " | |
| 63 | 1-Isopropylpyrrol-3-yl | H | " | —CH$_2$—CH=CH$_2$ | |
| 64 | 1-Isopropylpyrrol-3-yl (sodium salt) | H | " | " | |
| 65 | 1-Isopropylpyrrol-3-yl (sodium salt) | H | " | C$_2$H$_5$ | |
| 66 | 1-Isopropylpyrrol-3-yl (sodium salt) | H | C$_2$H$_5$ | " | |
| 67 | 1-Isopropylpyrrol-3-yl (sodium salt) | H | " | —CH$_2$—CH=CH$_2$ | |
| 68 | 1-Methylpyrazol-3-yl | H | " | " | |
| 69 | " | H | " | C$_2$H$_5$ | |
| 70 | " | COOCH$_3$ | n-C$_3$H$_7$ | " | n$_D^{24}$: 1.529 |
| 71 | " | " | " | —CH$_2$—CH=CH$_2$ | n$_D^{24}$: 1.530 |
| 72 | " | H | " | " | n$_D^{23}$: 1.546 |
| 73 | " | H | " | C$_2$H$_5$ | n$_D^{23}$: 1.541 |
| 74 | 1-Methylpyrazol-3-yl (sodium salt) | H | " | C$_2$H$_5$ | |
| 75 | 1-Methylpyrazol-3-yl (sodium salt) | H | " | —CH$_2$—CH=CH$_2$ | |
| 76 | 1-Methylpyrazol-4-yl | H | " | " | 63–66 |
| 77 | " | H | " | C$_2$H$_5$ | 80–84 |
| 78 | " | H | C$_2$H$_5$ | " | |
| 79 | " | H | " | —CH$_2$—CH=CH$_2$ | |
| 80 | " | COOCH$_3$ | n-C$_3$H$_7$ | " | n$_D^{23}$: 1.540 |
| 81 | " | " | " | C$_2$H$_5$ | n$_D^{23}$: 1.535 |
| 82 | 1-Methylpyrazol-4-yl (sodium salt) | H | " | " | |
| 83 | 1-Methylpyrazol-4-yl (sodium salt) | H | " | —CH$_2$—CH=CH$_2$ | |
| 84 | Pyrimid-2-yl | H | " | " | |
| 85 | " | H | " | C$_2$H$_5$ | |
| 86 | Pyrimid-2-yl (sodium salt) | H | " | " | |
| 87 | Pyrimid-4-yl | H | " | " | |
| 88 | Pyrimid-4-yl (sodium salt) | H | " | " | |
| 89 | Pyrimid-4-yl | H | " | —CH$_2$—CH=CH$_2$ | |
| 90 | 2-Methylpyrimid-4-yl | H | " | " | |
| 91 | " | H | " | C$_2$H$_5$ | |
| 92 | 2-Methylpyrimid-4-yl (sodium salt) | H | " | C$_2$H$_5$ | |
| 93 | 2,6-Dimethylpyrimid-4-yl | H | " | " | |
| 94 | 2,6-Dimethylpyrimid-4-yl (sodium salt) | H | " | " | |
| 95 | 2,6 Dimethylpyrimid-4-yl | H | " | —CH$_2$—CH=CH$_2$ | |
| 96 | Pyridazin-3-yl | H | " | " | |
| 97 | " | H | " | C$_2$H$_5$ | |
| 98 | Pyridazin-3-yl (sodium salt) | H | " | " | |
| 99 | Pyridazin-4-yl | H | " | " | |
| 100 | Pyridazin-4-yl (sodium salt) | H | " | " | |
| 101 | Pyridazin-4-yl | H | " | —CH$_2$—CH=CH$_2$ | |
| 102 | 2-Methylpyrid-5-yl | H | " | C$_2$H$_5$ | |
| 103 | 2-Methylpyrid-5-yl (sodium salt) | H | " | " | |
| 104 | 2-Methylpyrid-5-yl | H | " | —CH$_2$—CH=CH$_2$ | |
| 105 | 4-Methylpyrid-2-yl | H | " | " | |
| 106 | " | H | " | C$_2$H$_5$ | |
| 107 | 4-Methylpyrid-2-yl (sodium salt) | H | " | " | |
| 108 | 3-Methoxypyrid-2-yl | H | " | " | |
| 109 | " | H | " | " | |
| 110 | " | H | " | —CH$_2$—CH=CH$_2$ | |
| 111 | 2,6-Dimethoxy-4-methyl-pyrid-3-yl | H | " | " | |
| 112 | 2,6-Dimethoxy-4-methyl-pyrid-3-yl | H | " | C$_2$H$_5$ | |
| 113 | 2,6-Dimethoxy-4-methyl-pyrid-3-yl (sodium salt) | H | " | " | |

The substances according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated caster oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 10 parts by weight of compound no. 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 10 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 2 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 1 is intimately mixed with 95 parts by weight of particulate kaolin. A dust is obtained containing 5% by weight of the active ingredient.

VII. 30 parts by weight of compound no. 11 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 10 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The compounds may be applied preemergence, during emergence of the unwanted plants, or after emergence thereof.

The amount of active ingredient applied depends on the application method and the type and growth stage of the plants to be combated, and ranges from 0.025 to 10 kg/ha and more. The preferred application rate is from 0.1 to 1.5 kg/ha.

If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

In view of the many application methods possible, the herbicides according to the invention may be used in a very wide range of crops for removing unwanted plants.

The following crops may be mentioned by way of example:

| Botanical name | Common name |
|---|---|
| *Allium cepa* | onions |
| *Ananas comosus* | pineapples |

-continued

| Botanical name | Common name |
| --- | --- |
| *Arachis hypogaea* | peanuts (groundnuts) |
| *Asparagus officinalis* | asparagus |
| *Avena sativa* | oats |
| *Beta vulgais* spp. altissima | sugarbeets |
| *Beta vulgaris* spp. rapa | fodder beets |
| *Beta vulgaris* spp. esculenta | table beets, red beets |
| *Brassica napus* var. napus | rape |
| *Brassica napus* var. napobrassica | |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

(large plants:post-directed)

The action of the cyclohexane-1,3-dione derivatives of the formula I on the growth of plants from the Gramineae family and of broadleaved crop plants is demonstrated by greenhouse experiments. Crop plants from the Gramineae family may wither or be heavily damaged. In practice, this can in fact be desirable, as crop plants can become unwanted plants if they grow in another crop from seed remaining in the soil, e.g., voluntary barley in winter rape, or sorghum in soybeans.

The vessels employed were plastic flowerpots having a volume of 300 cm$^3$, and which were filled with a sandy loam containing about 1.5% humus. In the case of soybeans, peat was added to improve growth. The seeds of the test plants were sown shallow, and separately, according to species.

In the preemergence treatment, the active ingredients were applied to the surface of the soil as a suspension or emulsion in water by spraying through finely distributing nozzles. The amount of active ingredient applied in this treatment was equivalent to 0.125 or 3.0 kg/ha.

After the agents had been applied, the vessels were lightly sprinkler-irrigated to induce germination and growth. Transparent plastic covers were then placed on the vessels until the plants had taken root. The ocver ensured uniform germination of the plants, insofar as this was not impaired by the chemicals.

For the postemergence treatment, the plants were first grown in the vessels to a height of from 3 to 10 cm, depending on growth form, before being treated. In this method, the application rates were 0.125, 0.25 and 0.5 kg of active ingredient per hectare.

The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

To increase the spectrum of action and to achieve synergistic effects, the cyclohexane-1,3-dione derivatives of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Wetting agents, spreader-stickers, non-phytotoxic oils and oil concentrates may be also be added to initiate the herbicidal action.

We claim:

1. A cyclohexane-1,3-dione derivative of the formula

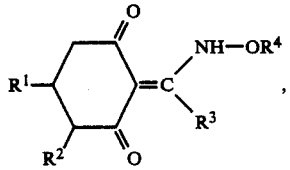

where $R^1$ is pyrazolyl group, and wherein said pyrazolyl group may also be substituted by one or two substituents from the group comprising alkyl of 1 to 3 carbons, halogen, or alkoxy of 1 or 2 carbons, $R^2$ is hydrogen, methoxycarbonyl or ethoxycarbonyl, $R^3$ is alkyl of 1 to 4 carbon atoms, and $R^4$ is alkyl of 1 to 3 carbon atoms, alkenyl of 3 or 4 carbon atoms, haloalkenyl of 3 or 4 carbon atoms and 1 to 3 halogen atoms, or propargyl, or a salt thereof.

2. A cyclohexane-1,3-dione derivative of the formula I as defined in claim 1, where $R^2$ is hydrogen, $R^3$ is alkyl selected from the group of ethyl, n-propyl and isopropyl, and $R^4$ is ethyl or allyl.

3. A compound of the formula I as defined in claim 1, wherein $R^1$ is N-methylpyrazol-3-yl.

4. A compound of the formula I as defined in claim 1, wherein $R^1$ is methylpyrazol-3-yl.

5. A compound of the formula I as defined in claim 1, wherein $R^1$ is 1-methylpyrazol-4-yl.

6. A herbidical composition containing inert additives and from 0.1 to 95 wt % of a cyclohexane-1,3-dione derivative of the formula I as defined in claim 1.

7. A herbicide containing inert additives and a cyclohexane-1,3-dione derivative of the formula I as claimed in claim 1, where $R^2$ is hydrogen, $R^3$ is alkyl selected from the group consisting of ethyl, n-propyl and isopropyl, and $R^4$ is ethyl or allyl.

8. A process for the control of unwanted plants, wherein the unwanted plants or the area to be kept free from unwanted plant growth is treated with a herbicidally effective amount of a cyclohexane-1,3-dione derivative of the formula I as defined in claim 1.

* * * * *